(12) United States Patent
Willmann et al.

(10) Patent No.: US 8,213,678 B2
(45) Date of Patent: Jul. 3, 2012

(54) SYSTEM AND METHOD OF ANALYZING THE MOVEMENT OF A USER

(75) Inventors: Richard Willmann, Siegburg (DE); Gerd Lanfermann, Aachen (DE); Andreas Brauers, Aachen (DE); Ralph Braspenning, Zundert (NL)

(73) Assignee: Koninklijke Philips Electronics N.V., Eindhoven (NL)

( * ) Notice: Subject to any disclaimer, the term of this patent is extended or adjusted under 35 U.S.C. 154(b) by 993 days.

(21) Appl. No.: 12/063,683

(22) PCT Filed: Aug. 9, 2006

(86) PCT No.: PCT/IB2006/052750
§ 371 (c)(1),
(2), (4) Date: Feb. 13, 2008

(87) PCT Pub. No.: WO2007/020568
PCT Pub. Date: Feb. 22, 2007

(65) Prior Publication Data
US 2010/0177933 A1    Jul. 15, 2010

(30) Foreign Application Priority Data
Aug. 19, 2005  (EP) .................................... 05107622

(51) Int. Cl.
*G06K 9/00* (2006.01)
(52) U.S. Cl. ....................................................... 382/103
(58) Field of Classification Search .................. 382/103, 382/100, 128; 600/595
See application file for complete search history.

(56) References Cited

U.S. PATENT DOCUMENTS

| 6,231,527 B1* | 5/2001 | Sol ................................. 600/595 |
| 6,816,603 B2 | 11/2004 | David et al. |
| 2003/0228033 A1* | 12/2003 | Daniel et al. .................. 382/104 |
| 2003/0233032 A1 | 12/2003 | Teicher et al. |

FOREIGN PATENT DOCUMENTS

| JP | 11099140 A | 4/1999 |
| WO | 0156471 A1 | 8/2001 |

(Continued)

OTHER PUBLICATIONS

DeHaan, G, et al., True motion estimation with 3D-recursive search block matching; 1993; IEEE Trans. on Circuits and Systems of Video Technology; 3(5)368-.

(Continued)

*Primary Examiner* — Claire X Wang

(57) ABSTRACT

The present invention relates to a system and method of analyzing the movement of a user. More particularly the present invention relates to a new technique for assessing a user's motor functions. It is an object of the present invention to provide a simple, robust, and low-cost technique for analyzing the movement of a user, which can be used in an unsupervised home environment. This object is achieved according to the invention by a method of analyzing the movement of a user, the method comprising the steps of causing the user to perform a coordinated movement in accordance with an instruction, generating video image data in form of a sequence of images by video recording the user, determining in the sequence of images a degree of synchronicity of optical flow on the left and right body half using a computer system comprising computer vision technology, and assessing the user's motor functions based on the degree of synchronicity.

17 Claims, 3 Drawing Sheets

FOREIGN PATENT DOCUMENTS

Figure 1:
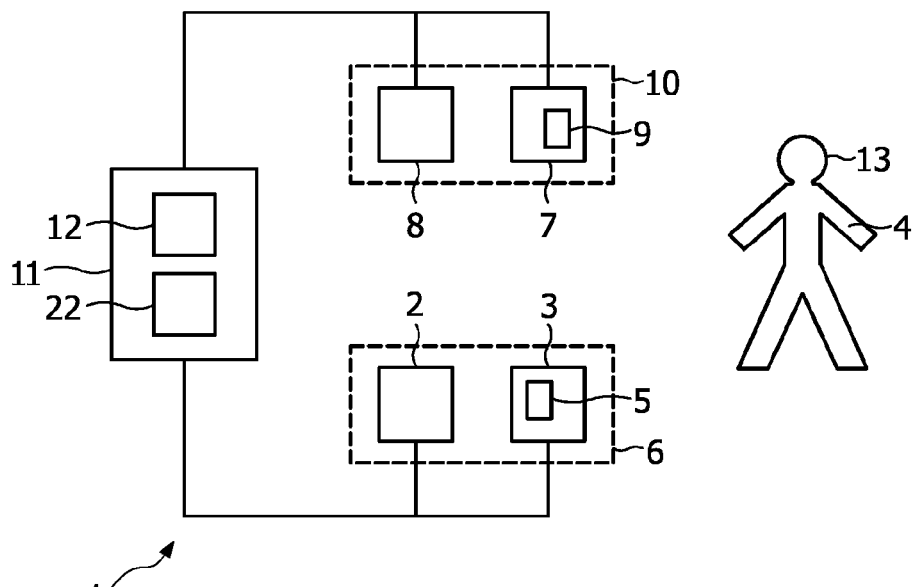

WO         02095714 A2    11/2002
WO     2005001768 A1    1/2005

OTHER PUBLICATIONS

Lu, C., et al.; Automated Analysis of Repetitive Joint Motion; 2003; IEEE Trans. on Information Technology in Biomedicine; 7(4)263-273.

Tao, Y., et al.; Building a Visual Tracking System for Home-Based Rehabilitation; 2003; Proc. of 9th Chinese Automation & Computing Soc. Conf. in UK; pp. 343-448.

Zhou, H., et al.; A Survey—Human Movement Tracking and Stroke Rehabilitation; Technical Report: CSM-420; 2004; University of Essex; pp. 1-32.

Jianghua Liu et al, "Dynamic Hand Gesture Recognition Based on Optical Flow", Computer Engineering, vol. 28, No. 4, Apr. 2002, pp. 104-105.

Gerard De Haan et al, "True-Motion Estimation With 3-D Recursive Search Block Matching", IEEE Transactions on Circuits and Systems for Video Techology, vol. 3, No. 5, Oct. 1993, pp. 368-379.

* cited by examiner

SYSTEM AND METHOD OF ANALYZING THE MOVEMENT OF A USER

The present invention relates to a system and method of analyzing the movement of a user. More particularly the present invention relates to a new technique for assessing a user's motor functions after a neurological insult, e.g. stroke Hemiparesis, i.e. a single-sided weakness of the limbs is a one of the most common impairments following stroke. In the US, 700.000 new cases of stroke occur per year. Deadly in 20% of the cases, stroke causes impairments in over 60% of the victims. Rehabilitation measures and loss of work force inflict costs of $50B to the US society per year.

To maximize rehabilitation efforts while optimizing costs it is desirable that rehabilitation exercises are continued by the patient at home without a supervising professional being available. It is well known that appropriate feedback enhances rehabilitation success. To this end, automatic assessment of exercises is necessary.

From the prior art different techniques of assessing motor impairments are known, e.g. by computerized evaluation of writing exercises, by strength measurements or by exercising on an input device. These known systems and methods are not intended for home use but for a professional environment.

Other known techniques are based upon a video approach, using video image data of a user to assess the user's motor abilities. U.S. Pat. No. 6,816,603 B2 shows a method and apparatus for remote medical monitoring incorporating video processing, wherein a plurality of silhouettes is generated and combined to provide a motion portrait, from which finally motion characteristics are calculated. The complex video processing procedure, which has been suggested in said patent, include a substantial pre-processing and post-processing. Thereby the very complex task of body segmentation is performed.

It is an object of the present invention to provide a simple, robust, and low-cost technique for analyzing the movement of a user, which can be used in an unsupervised home environment.

This object is achieved according to the invention by a method of analyzing the movement of a user, the method comprising the steps of causing the user to perform a coordinated movement in accordance with an instruction, generating video image data in form of a sequence of images by video recording the user, determining in the sequence of images a degree of synchronicity of optical flow on the left and right body half using a computer system comprising computer vision technology, and assessing the user's motor functions based on the degree of synchronicity. Additionally an appropriate feedback can be given to the user in form of correction and/or evaluation.

The object of the present invention is also achieved by a system for analyzing the movement of a user, the system comprising: a display unit and/or an audio interface adapted for causing the user to perform a coordinated movement in accordance with an instruction, a video camera adapted for generating video image data in form of a sequence of images by video recording the user, a computer system comprising computer vision technology, said computer system being adapted for determining based on the video image data a degree of synchronicity of optical flow on the left and right body half, and an analyzing unit adapted for assessing the user's motor functions based on the degree of synchronicity.

The object of the present invention is also achieved by a computer program for analyzing the movement of a user, the program comprising computer instructions to determine in the sequence of images a degree of synchronicity of optical flow on the user's left and right body half, wherein said video image data in form of a sequence of images are generated by video recording the user, and computer instructions to assess the user's motor functions based on the degree of synchronicity, when the computer program is executed in a computer. The technical effects necessary according to the invention can thus be realized on the basis of the instructions of the computer program in accordance with the invention. Such a computer program can be stored on a carrier such as a CD-ROM or it can be available over the internet or another computer network. Prior to executing the computer program is loaded into the computer by reading the computer program from the carrier, for example by means of a CD-ROM player, or from the internet, and storing it in the memory of the computer. The computer includes inter alia a central processor unit (CPU), a bus system, memory means, e.g. RAM or ROM etc., storage means, e.g. floppy disk or hard disk units etc. and input/output units. Alternatively the inventive method could be implemented in hardware, e.g. using one or more integrated circuits.

A core idea of the invention is to assess the user's motor functions based on a degree of synchronicity of the left and right half of the user's body. As a measure the synchronicity of optical flow on the left and right half of the user's body is used. In other words, the motion flow in a sequence of images is evaluated in a way that the synchronicity of the user's motions is used as a decisive criterion. According to the invention, it is not relevant for assessing the user's motor functions, whether the computer identifies a certain part of the video image as a user's hand or elbow etc. The computer system analyzes the video data solely with respect to the optical flow. No segmentation or other complex, time consuming and expensive tasks are necessary. Hence the system fulfills the requirements for robust operation in a home environment.

It has to be pointed out, that wherever the term synchronicity is used, the term asynchronicity might be used accordingly. In other words, it is not important for the invention, whether a degree of synchronicity or a degree of asynchronicity is determined while performing the method according to the invention. The aim is to determine, whether the movements of e.g. the user's upper limbs are synchronistic (i.e. simultaneous) and/or to which degree the are not synchronistic. With the invention different kinds of movements can be evaluated, e.g. movements of the upper and lower limb or movements of the user's face.

The new method and system according to the invention is characterized in that: it is not necessary for the user to carry reflective markers or the like, the lighting conditions must not be known, the user's clothing must not be known, and the user may position itself freely within the operating area of the camera. Therewith the main problems of the prior art techniques are solved. Additionally these advantages can be achieved by means of a simple, robust, and low-cost technique, usable in an unsupervised home environment.

These and other aspects of the invention will be further elaborated on the basis of the following embodiments which are defined in the dependent claims.

According to a preferred embodiment of the invention the user is instructed by means of a display unit and/or an audio interface. Thus, the user receives instructions to perform a certain physical task, e.g. a coordinated movement of the upper limbs. Preferably the requested task is shown to the user on the display unit and/or transmitted to the user via the audio interface, e.g. spoken by a speech synthesizer. Furthermore the display unit is preferably adapted for providing visual feedback at the end of the exercise or during the course of exercise, whereas the audio interface is preferably adapted for providing audio feedback to the user. In other words the display unit and/or the audio interface are adapted to provide the result of the assessment to the user.

According to the invention the degree of synchronicity is determined based on the optical flow on the left and right half of the user's body. In order to distinguish between the left and right body half, the centerline of the user's body is determined by tracking the user's face, according to another preferred embodiment of the invention. For this purpose a tracking software is used in combination with a movable video camera (which is equipped with servo motors to allow pan and tilt motions). This allows the user to move freely within the operation range of the video camera during the motor function test. In other words, computer vision technology in combination with a motor unit is employed to track the user and to position the camera such that the vertical midline of the user's body coincides with the midline of the images, where determining the vertical body midline can be achieved by tracking software for features such as the face and other body parts. Alternatively the task of determining the vertical body midline can be achieved by tracking body attached physical markers.

For determining the degree of synchronicity, video image data, which is assigned to the left of the centerline by means of the computer vision technology, is associated to the left body half of the user and video image data, which is assigned to the right of the centerline by means of the computer vision technology, is associated to the right body half of the user.

According to another preferred embodiment of the invention the recorded video images are segmented into static and moving areas. To determine the degree of synchronicity the flow components in the left and right half of the user's body are computed and compared to each other. For computing the flow components preferably a three frame 3D recursive search motion estimation algorithm is used. This kind of algorithm describes the user's motion by displacement vectors and allows an easy and direct analysis of the user's movements.

After the degree of synchronicity is calculated, an assessment of the user's motor function is performed. For this purpose the degree of synchronicity is compared with a threshold value, according to another preferred embodiment of the invention. Thereby the threshold value is either a static value, enabling the determination of severity of paralysis of e.g. the user's upper limbs. Alternatively the threshold value is adapted dynamically, thus the user's progress of motor rehabilitation can be determined, e.g. during a period of days or months.

Finally, according to yet another preferred embodiment of the invention, the result of the assessment are announced to the user, preferably using the display unit adapted to provide visual feedback to the user and/or an audio interface to provide audio feedback to the user.

Figure 2:
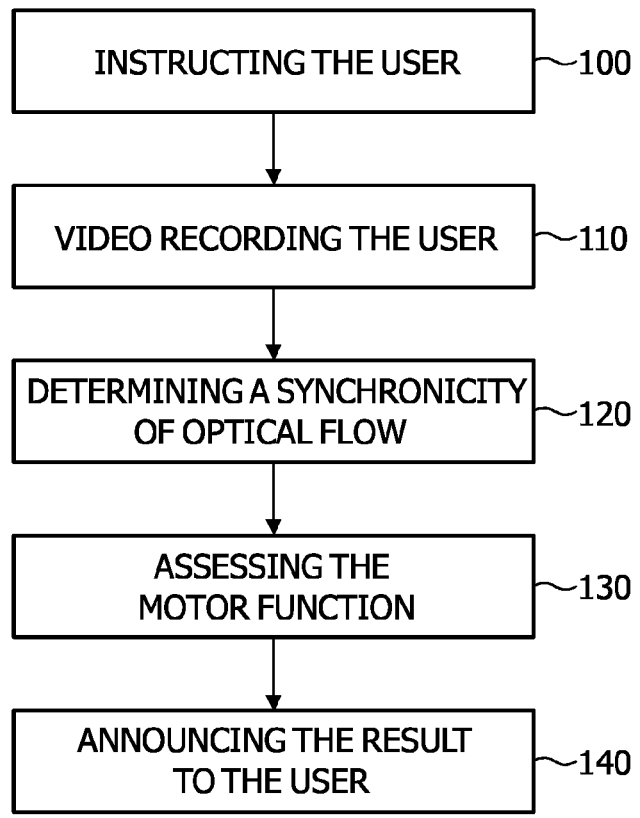
Figure 3:
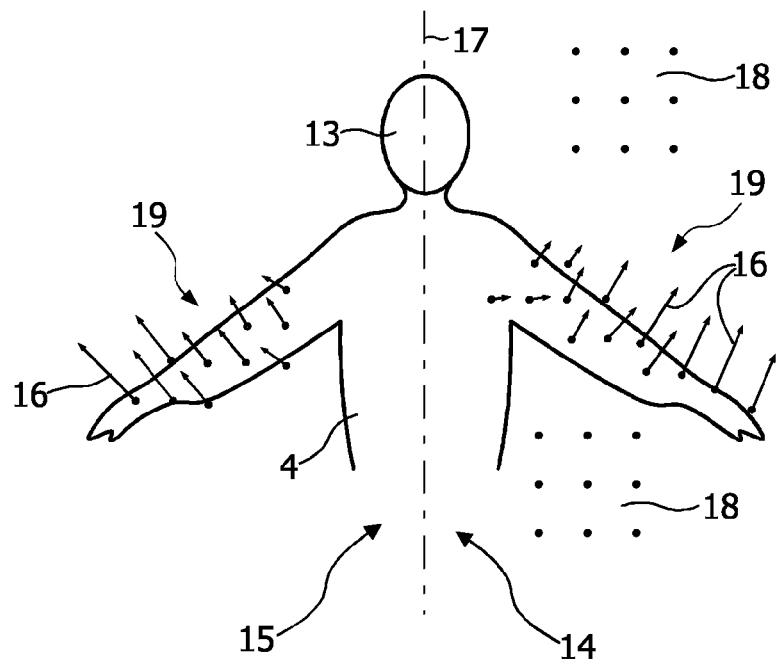
Figure 4:
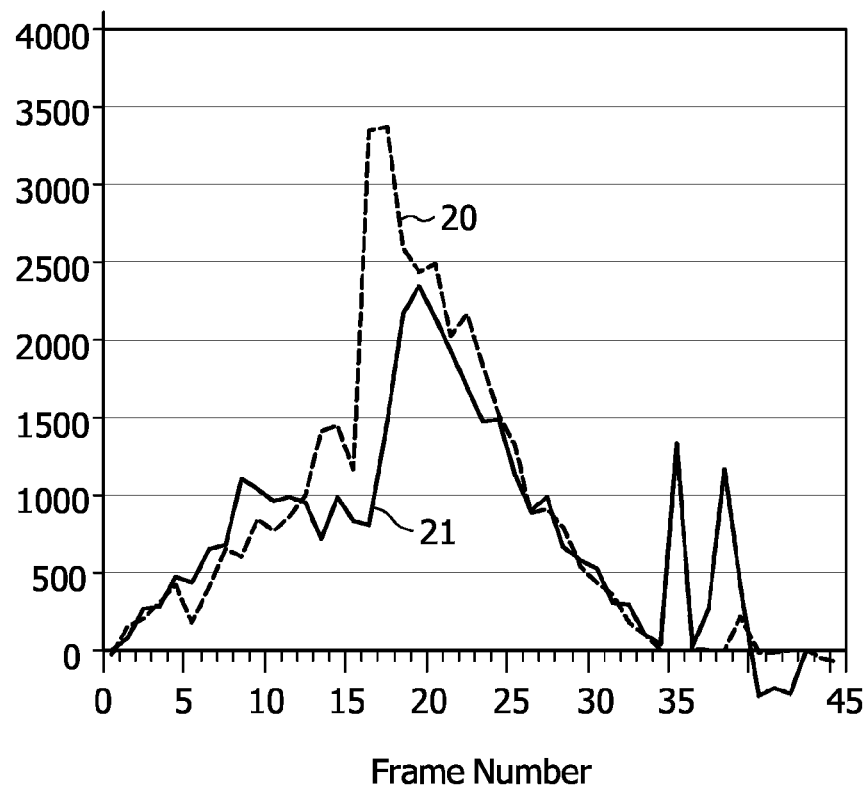
Figure 5:
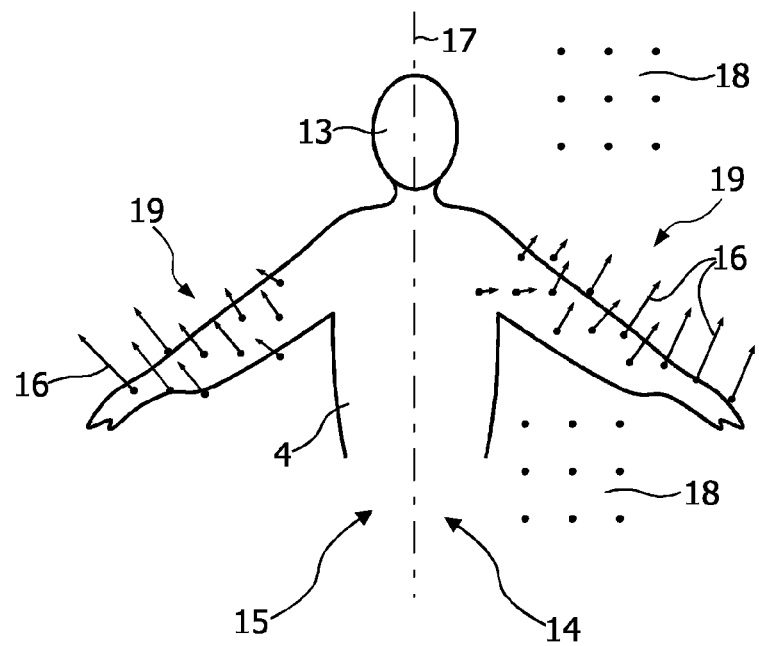
Figure 6:
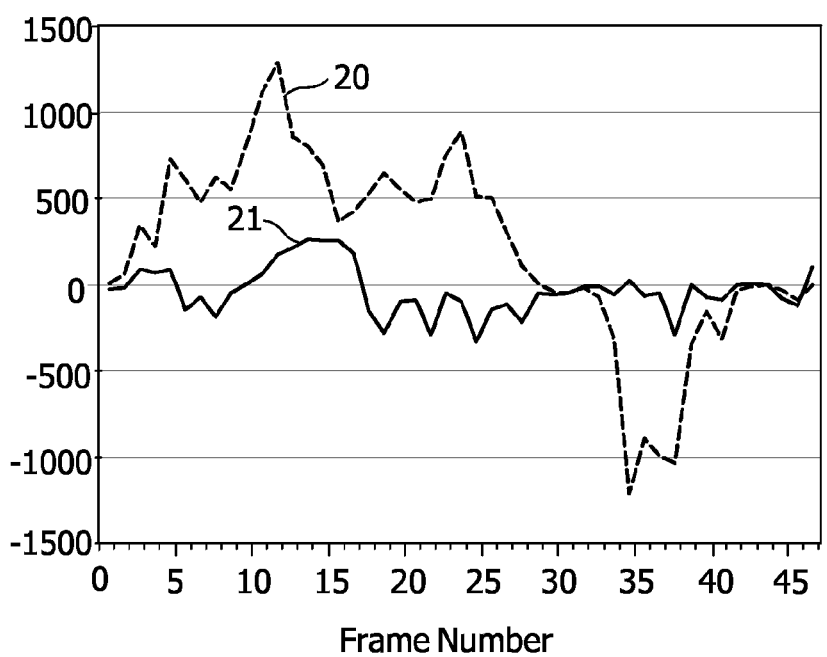

These and other aspects of the invention will be described in detail hereinafter, by way of example, with reference to the following embodiments and the accompanying drawings; in which:

FIG. 1 shows a schematic block diagram of a system according to the invention, FIG. 2 shows a simplified flowchart of the method according to the invention, FIG. 3 shows a schematic picture of a user with synchronously moving arms, FIG. 4 shows a diagram illustrating a synchronous arm movement, and FIG. 5 shows a schematic picture of a user with asynchronously moving arms, FIG. 6 shows a diagram illustrating an asynchronous arm movement.

The system 1 comprises a display unit 2 and an audio interface 3 adapted for causing the user 4 to perform a coordinated movement in accordance with an instruction (step 100). In other words the system 1 comprises means for instructing the user 4 about the exercise to perform. The user 4 is requested to perform a certain motion, e.g. a simultaneous raising and lowering of the arms. The instruction is given to the user 4 e.g. in form of a short video clip or animation by means of the display 2 and/or as a spoken instruction via a speaker 5. The display 2 and the audio interface 3 are preferably combined forming an interface unit 6. As interface unit 6, e.g. a computer monitor, a TV set, a handheld device or the like is used. The interface unit 6, in particular the display 2, is adapted for providing visual feedback to the user 4 during the exercise and/or at the end of the test. The feedback given during the exercise can include an information whether or not the exercise is being performed well by the user. The feedback given to the user 4 at the end of the test can include information about the results of the test.

The system 1 further comprises a video camera 7 adapted for generating video image data in form of a sequence of images by video recording the user 4 (step 110). For the purpose of the invention a single video camera 7 is sufficient. However, two or more video cameras 7 can be used, making the video image processing more complex. As video camera 7 a very simple standard camera can be used, for example a Philips ToU Cam. Such a video camera 7 allows the recording of video images with low or medium resolution, which is sufficient for the purpose of the present invention. The video camera 7 is equipped with a motor unit 8 comprising servo motors to allow pan and tilt motions of the camera lens. Video camera 7 and motor unit 8 are combined forming a camera unit 10. Such a video camera 7 is known for example from the Philips Home Dialog System.

In a very simple embodiment of the invention a TV set is used to serve as the interface unit 6 and for audio input, e.g. instructions spoken by the user, the built-in microphone 9 of the video camera 7 is used. In another embodiment (not shown) the display 2, the audio interface 3 and the video camera 7, 8 is combined forming a single device. This allows an easy operation of the system, especially for elderly people, since the system works without an extensive cabling.

The system 1 further comprises a computer system 11, implementing, among others, computer vision technology. The computer system 11, e.g. a standard personal computer, is adapted for carrying out the controlling of the inventive system 1. For this purpose the computer system 11 is connected with the camera unit 10 and the interface unit 6. From the video camera 7, the image sequence is transferred to the processing unit 12 of the computer system 11.

Furthermore the computer system 11 is adapted for performing all task of calculating and computing video image data as well as determining and assessing results. This is achieved according to the invention by means of a computer software comprising computer instructions adapted for carrying out the steps of the inventive method, when the software is executed in the computer system 11.

The computer system 11 comprises functional modules or units, which are implemented in form of hardware, software or in form of a combination of both.

A first unit of the computer system 11, which is preferably implemented as a software unit, is adapted to start the video recording following a user command to start the test. In other words, if the user 4 speaks a predefined START instruction, and this instruction is recorded by means of the microphone 9, the performed user motion is recorded by means of the video camera 7. During the recording the animation showing the requested motion is shown on the display 2.

A second unit of the computer system 11, which is preferably implemented as a software unit, is adapted to control the motor unit 8 such that the video camera 7 follows the user's face 13. Thereby the motor unit 8 is employed to track the user's face 13 and to position the video camera 7 such that the centerline of the user's body coincides with the centerline of the images.

While the camera image is being captured, the image is centered on the user's face midline (virtual centreline 17) due to the face tracking software and the pan/tilt function of the video camera 7. Therefore, left and right half of the image correspond to left and right half 14, 15 of the user's body. The pan/tilt function is used to track the user 4 before the exercise recording starts. During the video recording, this function is switched off and the user 4 is assumed to be standing in his place.

After the image sequence is recorded, the images are processed within the processing unit 12 of the computer system 11 (step 120). This processing unit 12 is preferably implemented as a software unit, but can of course also be implemented in form of a hardware unit. The processing unit 12 is adapted to compute the optical flow in the recorded image sequence, i.e. the unit is adapted to determine based on the video image data a degree of synchronicity of optical flow on the left body half 14 and right body half 15, see FIG. 3. For this purpose a specific algorithm is used to compute the flow in the recorded image sequence.

The algorithm for processing the image is the 3d-recursive search block matching algorithm as described by Gerard de Haan et al, "True motion estimation with 3D-recursive search block matching" in "IEEE transactions on circuits and systems of video technology", volume 3, number 5, October 1993, pages 368 et seqq., to which this application explicitly refers to and which is incorporated by reference. This algorithm is extremely efficient in comparison to other known block matching algorithms, which in principle allows the processing of the recorded images in real-time.

Furthermore, a variation of the algorithm known as "3-frame block matching" is employed. The name refers to the fact that the current camera image is being compared to the one before and the one thereafter and corresponding pixel blocks are searched for in forward and backward time direction by means of the processing unit 12. This avoids the occlusion problem and allows the segmentation of the image in moving foreground 19 and static background 18 without a previously built background model. This fact is important in this case as due to the pan/tilt function of the video camera 7 no information about the background can be gathered before the exercise recording starts.

Resulting from applying the above mentioned algorithm by means of the processing unit 12 is a flow field corresponding to the captured image. This means that for each block of pixels in the image, the displacement with respect to the previous image is stored by the processing unit 12 as a two dimensional vector $f(x,y,t)$ 16, where x and y are the pixel coordinates and t is the time at which the camera image was being captured, where $t=0$ is the start of the recorded sequence and $t=T$ is the end time. In other words this algorithm describes the user's motion by displacement vectors 16. Examples for such displacement vectors are shown in FIG. 3. The algorithm compares blocks of pixels within a number of video images. For this purpose the algorithm detects in an image a specific block of pixels (e.g. 3×3 pixels), which is already known to the algorithm from a previous image. The displacements vectors 16 define the displacements of this block of pixels, thus defining the optical flow. However, the algorithm does not know, whether a block of pixels shows an arm or an elbow of the user 4.

Given the flow field $f(x,y,t)$, the total flow $FL(t)$ and $FR(t)$ in the left and right half of the image are computed by means of the processing unit 12 by summing up the all $f(x,y,t)$ of pixels in the left and right half of the image, respectively. $FL(t)$ and $FR(t)$ are two-dimensional vectors having the x and y components of the total optical flow on the respective side as entries.

The sum of the movements in the left and right half of the image over the complete motion sequence $FL_{tot}$ and $FR_{tot}$ are computed by means of the processing unit 12. If the absolute value of either of these two values falls below a predefined threshold, it is concluded by the processing unit 12 that no movement took place on the respective side. This can lead either to repetition of the whole exercise or to the conclusion that the patient is not able to conduct a movement on one side.

Given the time series $FL(t)$ and $FR(t)$ where t is between 0 and T, the synchronicity of the movement is being assessed. To this end, the correlation coefficients of the x and y components of the time series $FL(t)$ and $FR(t)$ are computed by means of the processing unit 12, these quantities are being called Cx and Cy. By definition of the correlation coefficient Cx and Cy have values between −1 and 1. Here, a value of 1 means synchronicity, −1 means anti-synchronicity. If Cx and Cy are 0, movements that are not synchronized.

The correlation coefficient $C_{AB}$ of two scalar quantities $A(t)$ and $B(t)$ given the standard deviation of $A(t)$ as $S_A$ and that of $B(t)$ as $S_B$ is defined as $C_{AB}=(<AB>-<A><B>)/(S_A S_B)$. Here the brackets stand for mean values over the time series.

For a synchronous movement on the two body sides it is expected that the movement and thus the optical flow in the x direction is anti-synchronous, i.e. it is expected that correlation coefficient $Cx=-1$. For the movement in y-direction, synchronous movement is expected, i.e. $Cy=1$. Therefore, $C=|-1-Cx|+|1-Cy|$ is a scalar measure for the deviation from the synchronous movement. Here || denotes the absolute value.

Due to either a predefined threshold or a personalized threshold, the value C (correlation coefficient) obtained from the motion can be judged as describing a movement that is according to expectations or not.

A diagram illustrating a symmetric arm movement according to the user 4 illustrated in FIG. 3 is shown in FIG. 4. The diagram shows the sum of all motion vectors over the number of video frames for the Y-component of the left side flow vector 20 and Y-component of the right side flow vector 21. Both curves are nearly identically. The correlation coefficient Cy for this example is 0.82, indicating a symmetric (synchronous) arm movement of the user 4. The correlation coefficient serves as a measure of synchronicity.

FIG. 6 shows a diagram illustrating an asymmetric arm movement according to the user 4 illustrated in FIG. 5, where the correlation coefficient Cy is 0.21, indicating a asymmetric (asynchronous) arm movement of the user 4. As it can clearly be seen, the user's right arm has performed the requested exercise not very well. The right arm of the user performed almost no movement. As an result the right body half 15 shows a different motor behaviour as the left body half 16 and the computed correlation coefficient 16 is different from the example illustrated in FIG. 4.

Since the correlation factor is calculated based only on the optical flow, this method is robust with respect to a variety of lighting conditions, background and garment of the patient. The system detects the synchronicity of the movements without requiring the user 4 to wear markers or hold devices. No segmentation of the user's body into different body parts is necessary. Also the position of parts of the user's body is not relevant.

After the degree of synchronicity is calculated, an assessment of the user's motor function is performed (step 130). For this purpose an analyzing unit 22 of the computer system 11, which again is preferably implemented as a software unit, is adapted for assessing or grading the requested exercise, i.e. for assessing the user's motor functions based on the degree of synchronicity. The degree of synchronicity, i.e. the correlation factor, is compared with a threshold value, which is stored within the computer system 11.

Having data from a group of stroke victims and a healthy control group, a static threshold is defined for assessing the result of the motion estimation analysis. Alternatively the degree of synchronicity of each test is stored and the threshold value is adapted dynamically. In this case the degree of synchronicity serves as a progress indicator for rehabilitation. In this embodiment the analysing unit is especially trained to grade the performance of the individual user. It uses recorded historical data to evaluate the current performance in comparison with previous ones. This personalized algorithm allows the grading of rehabilitation success as well as reliable detection of relapse or recurrence of stroke events. The result of the assessment is announced to the user 4, preferably using the display 2 and/or the audio interface 3 (step 140).

If the analysis of the video image data results in an invalid conclusion or if no feasible results are determined, e.g. because the system is unable to perform the tracking of the user's face 13 etc., a new instruction is given from the computer system 11 to the user 4 via the interface unit 6, e.g. asking the user to repeat the last exercise. However, because of the robustness of the algorithm employed, movements of the user 4 during recording of the video images, e.g. a slight rotation of the user or the like, have no effect of the overall results and can therefore be neglected in most cases.

The current invention can be used as part of a home stroke test application. Such an application is preferably adapted to be a part of a telemedicine and e-health platform.

In contrast to prior art systems the current invention presents a realization of a system for assessing exercises for hemiparesis without any additional sensors or input devices except a video camera 7. Furthermore it provides the patient with visual feedback. The requested exercises are performed freely by the user 4 and recorded by the camera 7. After processing the images, assessment and feedback are given. Due to its robustness and the use of only low-cost standard computer equipment it is especially apt for use in an unsupervised home environment.

It will be evident to those skilled in the art that the invention is not limited to the details of the foregoing illustrative embodiments, and that the present invention may be embodied in other specific forms without departing from the spirit or essential attributes thereof. The present embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein. It will furthermore be evident that the word "comprising" does not exclude other elements or steps, that the words "a" or "an" do not exclude a plurality, and that a single element, such as a computer system or another unit may fulfil the functions of several means recited in the claims. Any reference signs in the claims shall not be construed as limiting the claim concerned.

REFERENCE NUMERALS

1 system
2 display
3 audio interface
4 user
5 speaker
6 interface unit
7 video camera
8 motor unit
9 microphone
10 camera unit
11 computer system
12 processing unit
13 user's face
14 left body half
15 right body half
16 displacement vector
17 centerline
18 static area
19 moving area
20 left side flow vector
21 right side flow vector
22 analyzing unit

What is claimed is:

1. A method of analyzing the movement of a user, comprising the steps of:
   instructing the user to perform a coordinated movement,
   generating video image data in form of a sequence of images by video recording the user (4),
   determining in the sequence of images a degree of synchronicity of optical flow between the left and the right body halves using a computer system comprising computer vision technology, and
   assessing the user's motor functions based on the degree of synchronicity.

2. The method as claimed in claim 1, wherein the step of instructing the user to perform a coordinated movement comprises the step of instructing the user using a display and/or an audio interface.

3. The method as claimed in claim 1, wherein the coordinated movement is a coordinated movement of the upper limbs.

4. The method as claimed in claim 1, wherein the step of determining a degree of synchronicity of optical flow on the left and right body half comprises the step of segmenting an image into static and moving areas.

5. The method as claimed in claim 1, wherein the step of determining a degree of synchronicity of optical flow on the left and right body halves comprises the step of comparing flow components in the left and right halves of the user's body.

6. The method as claimed in claim 1, wherein the step of determining a degree of synchronicity of optical flow on the left and right body halves comprises the step of determining based on the video image data a centerline of the user's body to define a left and right body half.

7. The method as claimed in claim 1, wherein the step of determining a degree of synchronicity of optical flow on the left and right body halves comprises the step of tracking the user's face.

8. The method as claimed in claim 1, wherein flow components are computed using a three frame 3D recursive search motion estimation algorithm.

9. The method as claimed in claim 1, wherein the step of assessing the user's motor functions comprises the step of comparing the degree of synchronicity with a threshold value.

10. The method as claimed in claim 1, wherein the step of assessing the user's motor functions comprises the step of determining a severity of paralysis.

11. The method as claimed in claim 1, wherein the step of assessing the user's motor functions comprises the step of determining the user's progress of motor rehabilitation.

12. The method as claimed in claim 1, comprising the further step of announcing the result of the assessment to the.

13. A system for analyzing the movement of a user, comprising:
   a display and/or an audio interface that instructs the user to perform a coordinated movement,
   a video camera that generates video image data in form of a sequence of images by video recording the user,
   a computer system comprising computer vision technology, said computer system determining, based on the video image data, a degree of synchronicity of optical flow between the user's left and right body halves, and
   an analyzing unit that assesses the user's motor functions based on the degree of synchronicity.

14. A non-transitory computer readable medium storing a computer program for analyzing the movement of a user, the program comprising:
   computer instructions to determine in the sequence of images a degree of synchronicity of optical flow between the user's left and right body halves, wherein said video image data in form of a sequence of images are generated by video recording the user,
   and
   computer instructions to assess the user's motor functions based on the degree of synchronicity,
   when the computer program is executed in a computer.

15. The system of claim 13 wherein the degree of synchronicity is determined by comparing flow components in the left and right halves of the user's body.

16. The system of claim 13 wherein the degree of synchronicity is compared to a threshold value.

17. The system of claim 13 wherein the analyzing unit provides an assessment of a severity of paralysis.

* * * * *